(12) United States Patent
Hill

(10) Patent No.: US 11,832,829 B2
(45) Date of Patent: Dec. 5, 2023

(54) STABILIZATION OF A TRANSSEPTAL DELIVERY DEVICE

(71) Applicant: Medtronic, Inc., Minneapolis, MN (US)

(72) Inventor: Alexander Hill, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 264 days.

(21) Appl. No.: 17/102,694

(22) Filed: Nov. 24, 2020

(65) Prior Publication Data

US 2021/0077117 A1 Mar. 18, 2021

Related U.S. Application Data

(62) Division of application No. 15/958,545, filed on Apr. 20, 2018, now abandoned.

(Continued)

(51) Int. Cl.
*A61M 25/00* (2006.01)
*A61F 2/24* (2006.01)
(Continued)

(52) U.S. Cl.
CPC .... *A61B 17/12122* (2013.01); *A61B 17/0057* (2013.01); *A61B 17/00234* (2013.01);
(Continued)

(58) Field of Classification Search
CPC .... A61B 17/12122; A61B 2018/00267; A61B 2018/00214; A61B 2018/0022;
(Continued)

(56) References Cited

U.S. PATENT DOCUMENTS 5,740,808 A * 4/1998 Panescu ............... A61B 5/6853
600/585
6,152,144 A * 11/2000 Lesh ................ A61B 17/12186
128/898

(Continued)

FOREIGN PATENT DOCUMENTS

DE 202010011492 12/2010
WO 00/27292 5/2000

(Continued)

OTHER PUBLICATIONS

International Search Report and Written Opinion for International Application No. PCT/US2018/028583 dated Jul. 5, 2018 (12 pgs.).

*Primary Examiner* — Martin T Ton
(74) *Attorney, Agent, or Firm* — Medler Ferro Woodhouse & Mills PLLC

(57) ABSTRACT

A transcatheter delivery device including a catheter and at least one stabilizer useful for transseptal procedures. The stabilizer includes a shaft connected to an anchor. The anchor has a delivery position in which the anchor is collapsed against the shaft and a deployed position in which the anchor expands to engage a pulmonary vein or atrial appendage to support the catheter within the septal wall as the catheter moves within a left atrium. Various disclosed delivery devices are also configured to ablate tissue proximate the anchor and/or can be disconnected from the delivery device after the procedure to occlude an atrial appendage. Methods of using the disclosed delivery devices and treating a heart are also disclosed.

19 Claims, 5 Drawing Sheets

Related U.S. Application Data

(60) Provisional application No. 62/487,836, filed on Apr. 20, 2017.

(51) Int. Cl.

| | | |
|---|---|---|
| *A61N 1/05* | (2006.01) | |
| *A61M 25/10* | (2013.01) | |
| *A61B 18/14* | (2006.01) | |
| *A61B 17/12* | (2006.01) | |
| *A61B 17/00* | (2006.01) | |
| *A61B 18/00* | (2006.01) | |

(52) U.S. Cl.
CPC ........ *A61B 18/1492* (2013.01); *A61F 2/2427* (2013.01); *A61M 25/0074* (2013.01); *A61M 25/1011* (2013.01); *A61N 1/056* (2013.01); *A61B 2017/00243* (2013.01); *A61B 2017/00292* (2013.01); *A61B 2018/00267* (2013.01); *A61B 2018/00357* (2013.01); *A61B 2018/00577* (2013.01); *A61M 2025/0079* (2013.01); *A61N 1/057* (2013.01)

(58) Field of Classification Search
CPC .. A61B 2018/0025; A61B 2018/00255; A61B 2018/00261; A61B 2018/00273; A61B 2018/00285; A61M 2025/0079; A61N 1/057

See application file for complete search history.

(56) References Cited

U.S. PATENT DOCUMENTS

| | | | |
|---|---|---|---|
| 6,314,962 B1 * | 11/2001 | Vaska | A61B 18/02 606/41 |
| 7,621,948 B2 | 11/2009 | Herrmann et al. | |
| 8,105,375 B2 | 1/2012 | Navia et al. | |
| 8,591,460 B2 | 11/2013 | Wilson et al. | |
| 8,900,214 B2 | 12/2014 | Nance et al. | |
| 9,078,994 B2 | 7/2015 | Rosenman et al. | |
| 10,368,989 B2 | 8/2019 | Duffy et al. | |
| 10,575,950 B2 | 3/2020 | McLean | |
| 2004/0215310 A1 * | 10/2004 | Amirana | A61B 18/14 623/1.11 |
| 2004/0260394 A1 | 12/2004 | Douk et al. | |
| 2006/0030885 A1 | 2/2006 | Hyde | |
| 2006/0069385 A1 | 3/2006 | Lafontaine et al. | |
| 2006/0241745 A1 * | 10/2006 | Solem | A61F 2/2457 623/2.18 |
| 2008/0243081 A1 * | 10/2008 | Nance | A61B 17/3439 604/164.03 |
| 2009/0018538 A1 | 1/2009 | Webster et al. | |
| 2010/0217382 A1 * | 8/2010 | Chau | A61F 2/2418 623/2.12 |
| 2011/0208297 A1 | 8/2011 | Tuval et al. | |
| 2012/0059458 A1 | 3/2012 | Buchbinder et al. | |
| 2013/0060328 A1 | 3/2013 | Rothstein | |
| 2013/0226290 A1 | 8/2013 | Yellin et al. | |
| 2013/0231735 A1 | 9/2013 | Deem et al. | |
| 2013/0310928 A1 | 11/2013 | Morriss et al. | |
| 2014/0012369 A1 | 1/2014 | Murry, III et al. | |
| 2014/0039611 A1 | 2/2014 | Lane et al. | |
| 2014/0276395 A1 | 9/2014 | Wilson et al. | |
| 2014/0350669 A1 | 11/2014 | Gillespie et al. | |
| 2014/0379074 A1 | 12/2014 | Spence et al. | |
| 2015/0018940 A1 | 1/2015 | Quill et al. | |
| 2015/0119981 A1 | 4/2015 | Khairkhahan et al. | |
| 2015/0238315 A1 | 8/2015 | Rabito et al. | |
| 2015/0238729 A1 * | 8/2015 | Jenson | A61M 25/04 604/510 |
| 2016/0015444 A1 * | 1/2016 | Wittenberger | A61B 18/02 606/21 |
| 2016/0242788 A1 | 8/2016 | Ibrahim et al. | |
| 2016/0374754 A1 * | 12/2016 | Asirvatham | A61B 18/02 606/41 |
| 2017/0333122 A1 | 11/2017 | Rajagopalan et al. | |
| 2018/0303488 A1 | 10/2018 | Hill | |
| 2020/0246069 A1 * | 8/2020 | Rioux | A61B 18/1206 |

FOREIGN PATENT DOCUMENTS

| | | |
|---|---|---|
| WO | 00/67832 | 11/2000 |
| WO | 02/094363 | 11/2002 |
| WO | 2011/129894 | 10/2011 |
| WO | 2015/073970 | 5/2015 |
| WO | 2018175220 | 9/2018 |

* cited by examiner

STABILIZATION OF A TRANSSEPTAL DELIVERY DEVICE

CROSS-REFERENCE TO RELATED APPLICATIONS

This application is a Divisional application of Ser. No. 15/958,545, filed on Apr. 20, 2018, entitled, "STABILIZATION OF A TRANSSEPTAL DELIVERY DEVICE," which claims the benefit of the filing date of U.S. Provisional Patent Application Ser. No. 62/487,836, filed Apr. 20, 2017, the entire teachings of which are incorporated herein by reference.

BACKGROUND

The present disclosure relates to devices and methods for stabilizing a device positioned within a septal wall of a human heart. More particularly, it relates to devices and methods for transseptally accessing a left atrium of a heart for delivery of an apparatus, such as a prosthesis, ablation apparatus or other apparatus.

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the mitral valve into the left ventricle. The left ventricle contracts and pumps blood through the aortic valve into the aorta and to the vascular system.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open-heart surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With these percutaneous transcatheter (or transluminal) techniques, a valve prosthesis is compacted for delivery in a catheter and then advanced, for example, through an opening in the femoral artery and through the patient's vasculature to the target site. A common approach for accessing the left side of the heart is a transseptal access from the right atrium through the intra-atrial septum and to the left atrium.

Other heart treatment procedures can be conducted via transseptal delivery of a transcatheter device. Such procedures can include heart tissue ablation for treatment of concomitant disease or delivery of an appendage plug for occluding a left atrial appendage, for example.

The disclosure addresses problems and limitations associated with related delivery devices for transseptally accessing a left atrium.

SUMMARY

One aspect of the present disclosure relates to a delivery device including a catheter and at least one stabilizer. In various embodiments, the catheter includes a plurality of lumens. One lumen optionally can serve as a passageway for a prosthesis or other apparatus to be delivered to the left atrium. Additional lumens can serve as a delivery conduit for respective stabilizers or other devices. During advancement of the delivery device through a septal wall, the stabilizers can be positioned within respective lumens. Once the delivery device is in position within the septal wall, an anchor of each stabilizer can be guided to and deployed to engage a pulmonary vein or a left atrial appendage to stabilize the delivery device, thus reducing the likelihood of damage to the septal wall as the catheter is navigated around the left atrium. In various embodiments, the stabilizer includes one or more ablation elements. In other embodiments, the stabilizer can be disconnected from the delivery device for implantation, for example, within the left atrial appendage to occlude the atrial appendage.

Another aspect of the present disclosure relates to methods of delivering an apparatus, such as a prosthesis, ablation or other apparatus, to the left atrium via transseptal delivery. The method includes providing a delivery system including a delivery device having a catheter and at least one stabilizer. After the delivery device is advanced through the septal wall, the stabilizer is deployed from the catheter to stabilize the delivery device with respect to the septal wall. In various embodiments, each stabilizer is deployed to engage one respective pulmonary vein. In other embodiments, one stabilizer is deployed to engage the left atrial appendage. In some embodiments, once the stabilizer is deployed, the prosthesis or other apparatus can be delivered through one respective lumen in the delivery device to the left atrium for treatment of the heart. In other embodiments, ablation is performed with the stabilizer, once deployed. Once a treatment procedure within the left atrium is complete, the stabilizer can optionally be disengaged from the respective anatomy, transitioned to the delivery position and then withdrawn from the patient along with the delivery device. Alternatively, the stabilizer can be disconnected from the delivery device and left within the patient (e.g., to occlude the left atrial appendage).

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
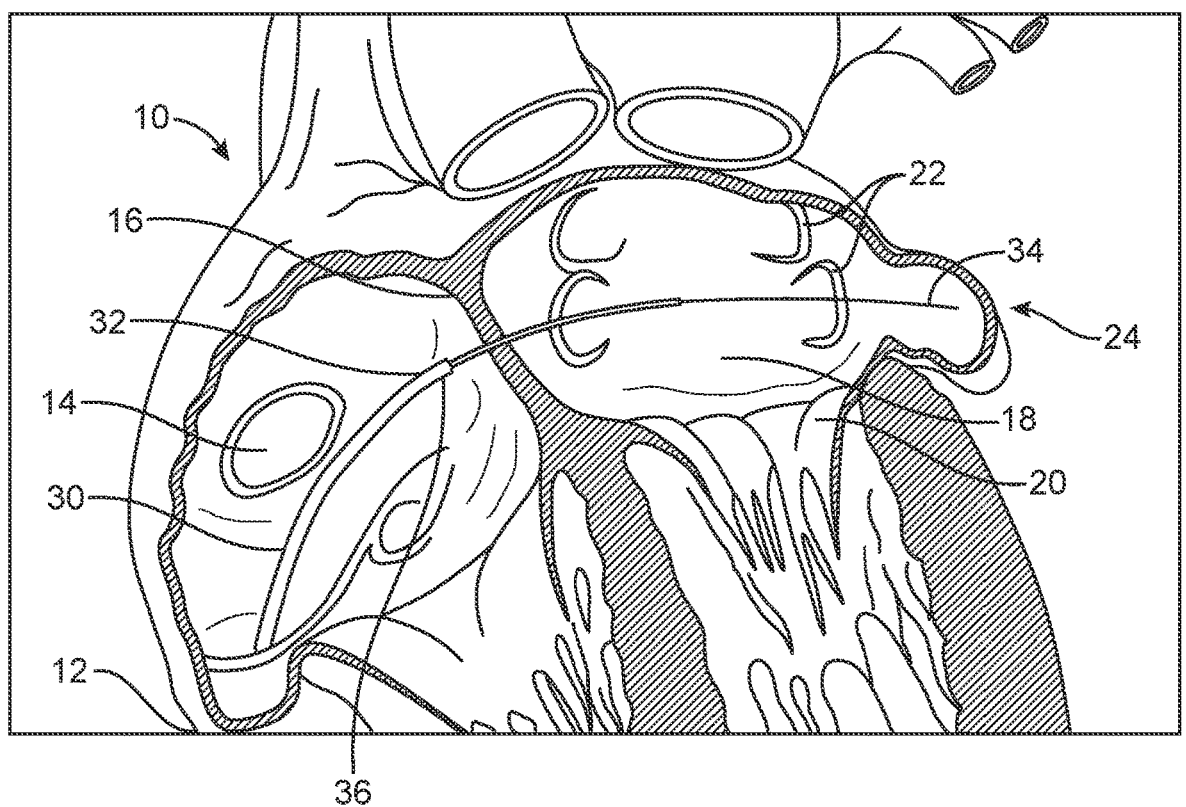
FIG. 1 is a cross-sectional illustration of a procedure for transseptally delivering an apparatus (not visible) to a left atrium of a human heart with a delivery device.

By way of background, one example of a treatment procedure for a human heart 10 including an inferior vena cava 12, right atrium 14, septal wall 16, left atrium 18 and a plurality of valves, including a mitral valve 20, is generally depicted in FIG. 1. In this example, a delivery device 30 including one or more coaxially arranged catheters 32 carrying an apparatus (not visible) is maneuvered over a guide wire 34, typically routed through the vena cava 12 to the right atrium 14 and to the patient's septal wall 16. The delivery path can continue transseptally through the patient's septal wall 16 to the left atrium 18 and resume, for example, by turning approximately 90° downward through the native mitral valve 20 or can travel to pulmonary veins 22 or a left atrial appendage 24, depending on the procedure. One of the difficulties in either positioning the prosthesis or other apparatus in the left atrium 18 or crossing the mitral valve annulus 20 with a transcatheter delivery device is stabilizing the delivery device 30 within the septal wall 16 during movement of the catheter 32. Although the point at which the catheter 32 passes through the septal wall 16 acts in some way as a stabilization point for the catheter 32, the septal wall 16 hole can be further damaged during the articulation of the catheter tip 36 into and through the left atrium 18. It is believed that the embodiments of the present disclosure will allow for atraumatic stabilization of a delivery device positioned within a septal wall causing less trauma to the septal wall as treatment is conducted. In addition, the disclosed stabilized delivery devices also provide for a more rigid backstop against which the distal tip of the delivery device can be steered. In further embodiments, the stabilizers disclosed herein can be configured to ablate pulmonary vein or left atrial appendage tissue. In addition, the stabilizers disclosed herein can also be configured to detach from the delivery device and occlude the left atrial appendage, as desired.

Figure 2:
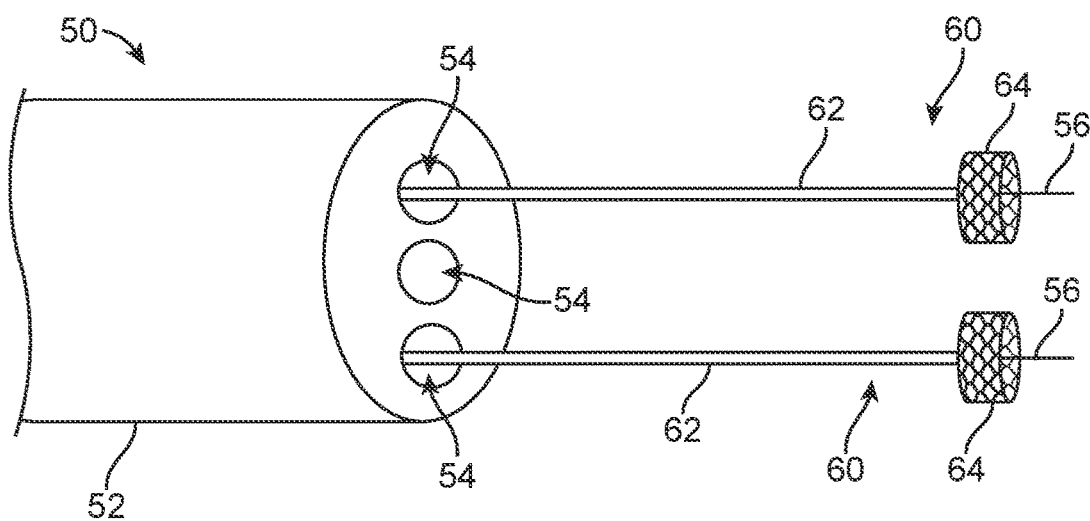
FIG. 2 is a partial, schematic illustration of a delivery device including a catheter and two stabilizers.

Turning now also to FIG. 2, which schematically illustrates a delivery device 50 having a catheter 52 (shown as truncated) including a plurality of lumens 54. The catheter 52 is shown as having three lumens 54, however, more or fewer lumens 54 can be provided. In this embodiment, two lumens 54 are provided for respective stabilizers 60. Each stabilizer 60 can include an actuating shaft 62 and an anchor 64 connected to a distal end 66 of the actuating shaft 62. In some embodiments, the anchor 64 is arranged and configured for engaging an inner surface of a respective pulmonary vein 22. In one example embodiment, each anchor 64 has an outer diameter in the range of about 9 mm to about 35 mm. The anchors 64 are shown as being cylindrical but can take other shapes. In addition, the anchor 64 can be configured to allow blood to flow through the respective pulmonary vein 22. For example, the anchor 64 can be generally tubular. Alternatively, the stabilizer can be arranged and configured for engaging an inner surface of a left atrial appendage 24. It may be desired to plug the left atrial appendage 24 after the delivery device is withdrawn from the patient and in this case, the anchor 64 can be configured to disengage from both the shaft 62 and delivery device 50 and the anchor 64 can further be configured to occlude the left atrial appendage 24, as will be discussed in detail below. The stabilizers 60 of the delivery device 50 can be of the same configuration or can have different configurations.

The disclosed stabilizers 60 can take a variety of configurations transitioning from a compressed, delivery arrangement to an expanded, deployed arrangement for engagement within a bodily lumen, such as one pulmonary vein 22 or atrial appendage 24. A few illustrative examples of how the stabilizers 60 can alternatively be configured are discussed below with respect to the remaining figures.

Figure 3A:
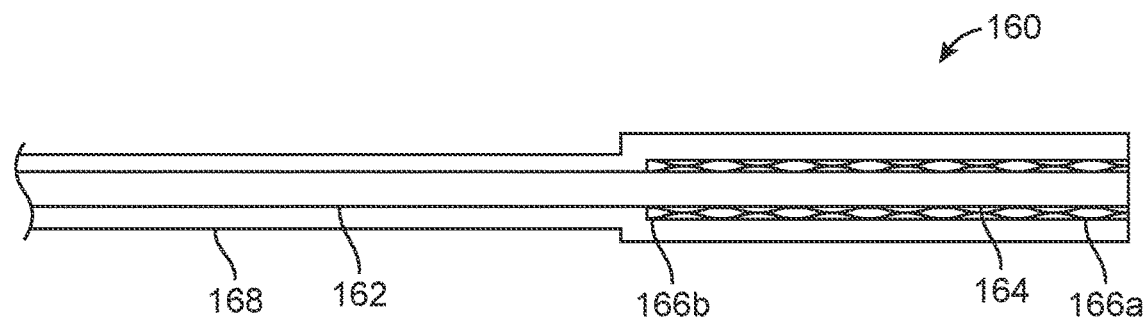
FIG. 3A is a partial, schematic illustration of a delivery device in a delivery position.
Figure 3B:
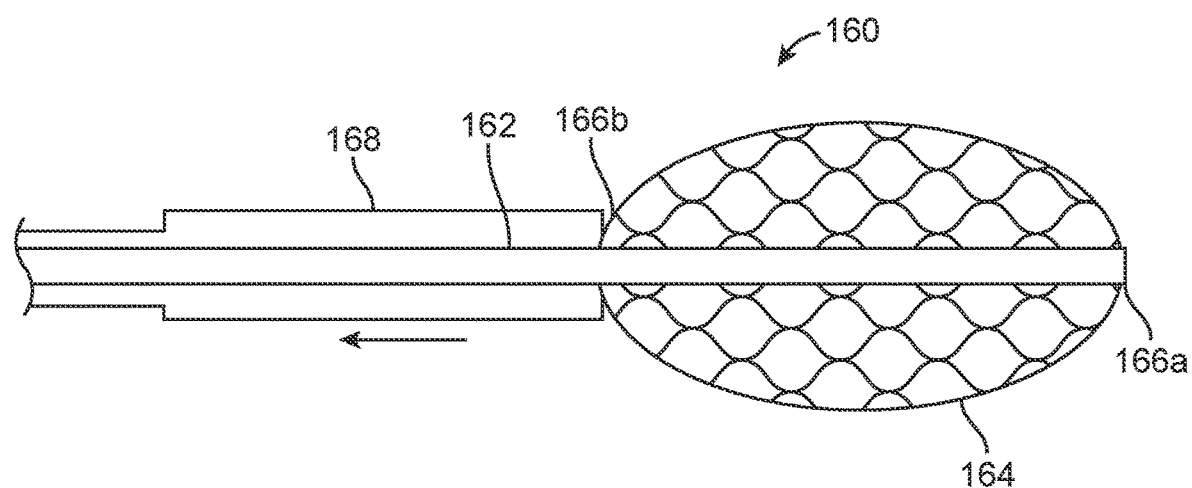
FIG. 3B is a partial, schematic illustration of the delivery device of FIG. 3A in a deployed position.

In one embodiment schematically illustrated in FIGS. 3A-3B, a stabilizer 160 can include an actuator shaft 162 attached to an anchor 164 that can be a metal mesh cage made of nitinol or the like that has shape memory and is biased to a deployed position (FIG. 3B). In one example embodiment, the anchor 164 has a greatest outer diameter in the range of about 9 mm to about 35 mm and can come in a multitude of sizes. A sheath 168 is provided over the anchor 164 in the delivery arrangement (FIG. 3A) to compress and retain the anchor 164 against its natural bias. Once the anchor 164 is positioned within the respective lumen of the anatomy, the sheath 168 can be proximally retracted to allow the anchor 164 to expand due to its natural bias. The anchor 164 is arranged and configured to expand and engage the anatomy, thus providing stability to the delivery device (see also FIGS. 1-2). Once the procedure is complete and the delivery device is to be withdrawn, the sheath 168 can be distally advanced over the anchor 164 to recapture and compress the anchor 164 within the sheath 168 for subsequent retraction and removal of the stabilizer 160 from the patient. The stabilizer 160 can be used with the delivery device 50 and the catheter 52 of FIG. 2 or an alternate delivery device.

Figure 4A:
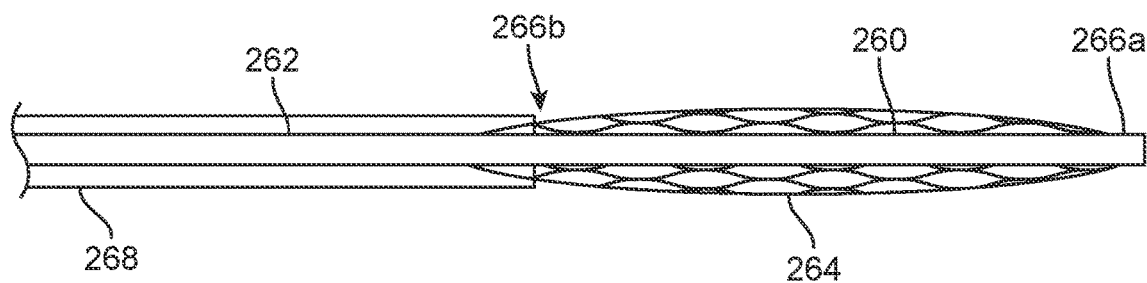
FIG. 4A is a partial, schematic illustration of an alternate delivery device in a delivery position.
Figure 4B:
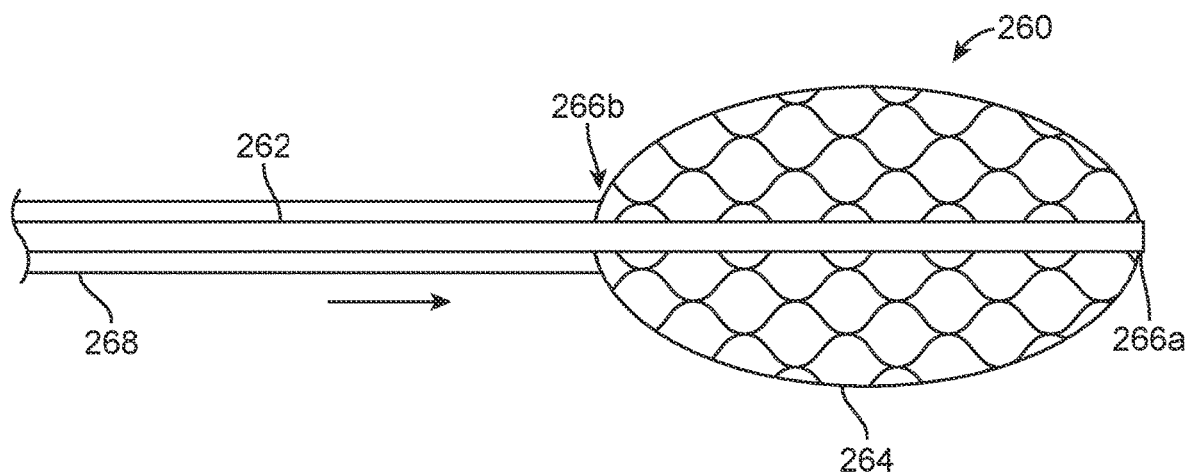
FIG. 4B is a partial, schematic illustration of the delivery device of FIG. 4A in a deployed position.

Yet another embodiment is illustrated in FIGS. 4A-4B, which shows a stabilizer 260 that can be used with the delivery device 50 and the catheter 52 of FIG. 2 or alternate delivery device. The stabilizer 260 includes an expandable anchor 264 interconnected to an actuating shaft 268, which are both positioned over a rod 262. In one example embodiment, the anchor 264 has a greatest outer diameter in the range of about 9 mm to about 35 mm and has any of the properties of the anchors 64, 164 disclosed above. A distal end 266a of the anchor 264 is fixedly secured to the rod 262 and a proximal end 266b of the anchor 264 is fixedly secured to the actuating shaft 268. In this embodiment, proximal retraction of the actuating shaft 268 correspondingly pulls the proximal end 266b of the anchor 264 proximally to correspondingly reduce the greatest outer diameter of the anchor 264. This delivery position is illustrated in FIG. 4A. To transition the anchor 264 into the deployed position of FIG. 4B, the actuating shaft 268 can be pushed distally to correspondingly push the proximal end 266b of the anchor 264 closer to the distal end 266a of the anchor 264, thus expanding the greatest outer diameter of the anchor 264 to engage the anchor 264 with the vessel lumen and stabilize the delivery device. Another option would be to configure the shaft 268 to be fixed and to use proximal and distal movement of the rod 262 as an actuator in a similar manner. For example, the rod 262 could be pushed distally with respect to the shaft 268 to collapse the anchor 264 and pulled proximally with respect to the shaft 268 to expand the anchor 264 (e.g., moving the distal end 266a farther or closer to the proximal end 266b). Once the treatment procedure is complete, the actuating shaft 268 can be proximally retracted to transition the anchor 264 back into the delivery position for withdrawal within the respective catheter lumen (see, e.g., catheter lumen 54 of FIG. 2).

Figure 5A:
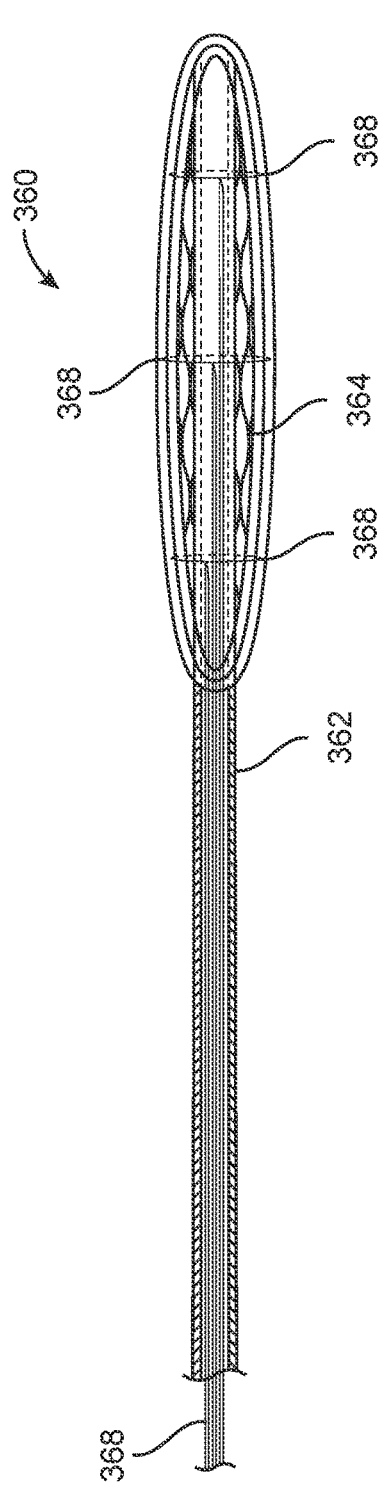
FIG. 5A is a partial, schematic illustration of another delivery device in a delivery position.
Figure 5B:
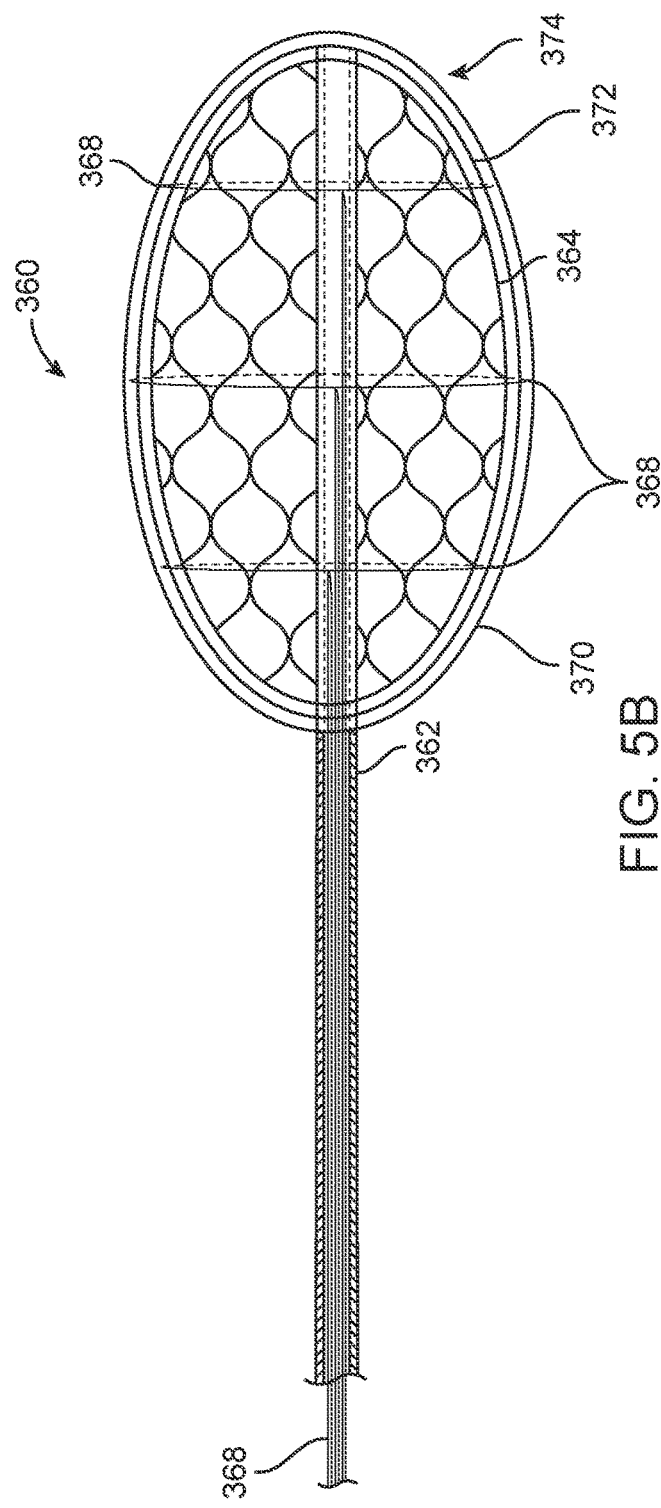
FIG. 5B is a partial, schematic illustration of the delivery device of FIG. 5A in a deployed position.

Referring also now to FIGS. 5A-5B, which illustrate an alternate stabilizer 360 that can be used with the delivery device 50 and the catheter 52 of FIG. 2 or other delivery device. The stabilizer 360 includes a shaft 362 interconnected to an expandable anchor 364. In one example embodiment, the anchor 364 has a greatest outer diameter in the range of about 9 mm to about 35 mm and has any of the properties of the anchors 64, 164, 264 disclosed above. A plurality of elongate tension members 368 extend along or through the shaft 362 and circumscribe the expandable anchor 364. Each tension member 368 can be woven through the anchor 364 to maintain the tension member 368 in position around the anchor 364. After wrapping around the anchor 364, each tension member 368 extends proximally back through the shaft 362. The tension members 368 are arranged and configured such that tension can be applied to the tension members 368 to compress and restrain the anchor 364 into the delivery position of FIG. 5A. The tension members 368 can be, for example, sutures, filaments, cables, cords or the like. In one example embodiment, three tension members 368 are provided. To deploy the anchor 364 into the deployed position of FIG. 5B, tension in the tension members 368 can be lessened, thus allowing a greatest outer diameter of the anchor 364 to expand, engage the vessel lumen and stabilize the delivery device. Once the treatment procedure is complete, the tension members 368 can again be tensioned to compress the anchor 364 back into the delivery position for withdrawal within the respective catheter lumen (see also, FIG. 2 and related disclosure).

As shown, the anchor 364 can optionally be housed within an outer, first balloon 370 and an inner, second balloon 372. Each tension member 368 is at least partially retained between the two balloons 370, 372 and functions in a similar manner as above in the embodiment where the balloons 370, 372 are not provided. The second balloon 372 includes one or more channels 374 through which the tension members 368 is routed to and from the anchor 364. The balloons 370, 372 are made of a compliant material so that they can expand along with the anchor 364. Suitable materials for balloons 370, 372 include nylon, Pebax® thermoplastic elastomers, polyurethane, or the like and provide a particularly atraumatic stabilizer 360.

Figure 6:
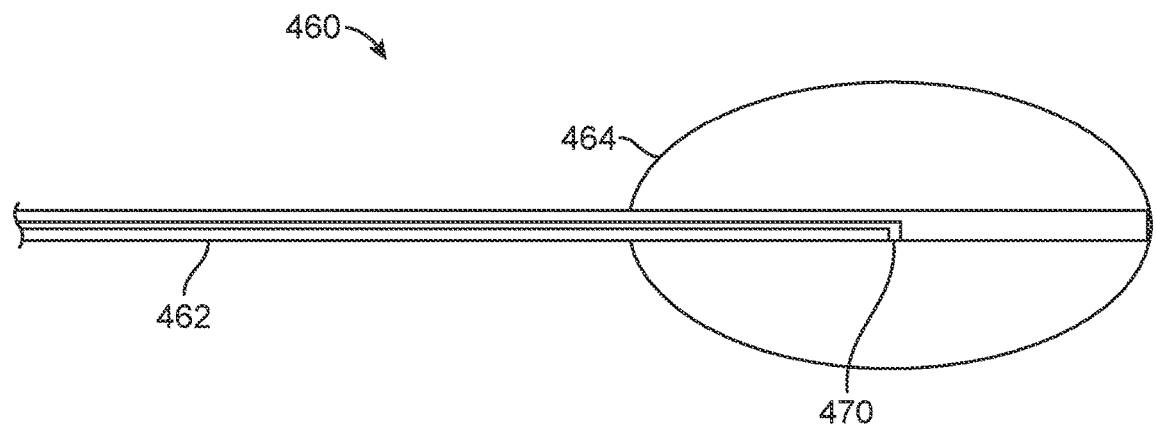
FIG. 6 is a partial, schematic illustration of an alternate delivery device in an inflated, deployed position.

Referring now also to FIG. 6, which illustrates an alternate stabilizer 460 that can be used with the delivery device 50 and the catheter 52 of FIG. 2. The stabilizer 460 includes a shaft 462 and an inflatable anchor 464. The inflatable anchor 464 can, for example be a compliant balloon that is either elliptical or spherical upon inflation and made of nylon, Pebax® thermoplastic elastomers, polyurethane, or the like. In one example embodiment, the anchor 464 has a greatest outer diameter in the range of about 9 mm to about 35 mm. To deploy the anchor 464 from a delivery position in which the anchor 464 is deflated (not shown) into the deployed position of FIG. 6 in which a greatest diameter of the anchor 464 is increased as compared to the delivery position, the anchor 464 can be inflated via an inflation channel 470 in the shaft 462 or otherwise until the anchor 464 engages a vessel lumen, such as a pulmonary vein or atrial appendage, to stabilize the delivery device. Once the treatment procedure is complete, the anchor 464 can be deflated to transition the anchor 464 back into the delivery position for withdrawal within the respective catheter lumen (see also, FIG. 2 and related disclosure).

Figure 7:
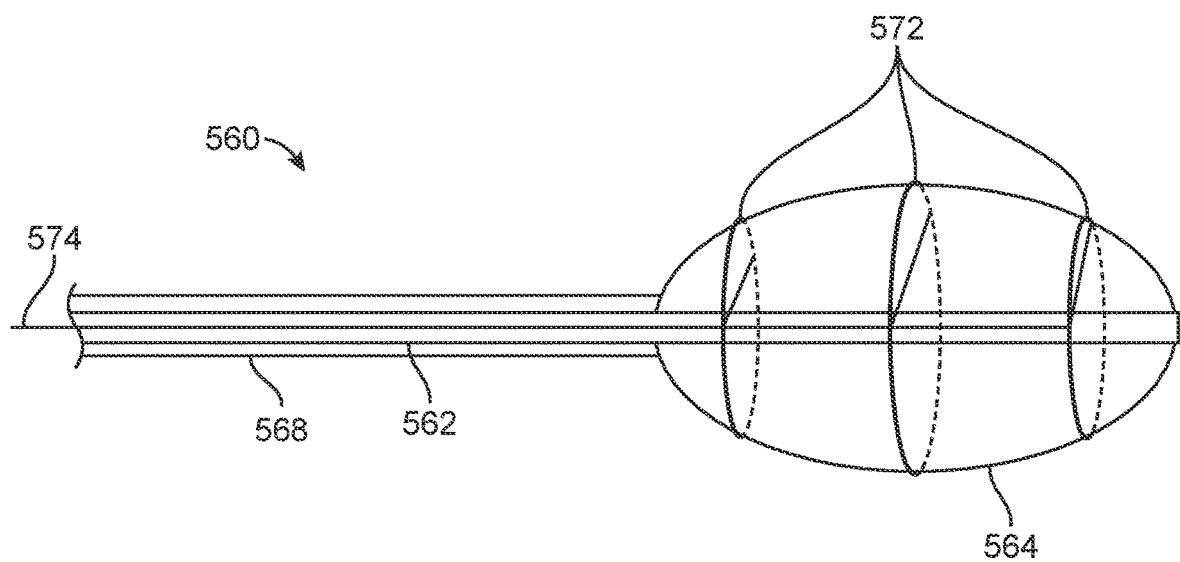
FIG. 7 is a partial, schematic illustration of another delivery device in a deployed position, the delivery device including an anchor having at least one ablation element.

As schematically illustrated in FIG. 7, all of the stabilizers disclosed herein can also optionally be configured to ablate tissue of the anatomy proximate which the stabilizer is engaged. In one example embodiment, a stabilizer 560 can include one or more ablation elements 572 positioned on an anchor 564 can be electrically connected to an ablation source via a wire 574 and configured to transfer ablation energy from the ablation source (not shown) to tissue (e.g., to the pulmonary vein 22 or atrial appendage 24 shown in FIG. 1). If multiple ablation elements 572 are positioned on each stabilizer 560, they may be configured to be individually energized so that deployment position of the stabilizer 560 does not have to be very precise. Fewer or more ablation elements 572 can be utilized, as desired. The stabilizer 560 can otherwise take any of the forms and can be actuated similarly to any other of the stabilizers disclosed herein. As one illustrated example, the anchor 564 can be positioned over a rod 562 and expansion and contraction of the anchor 564 can be controlled with a shaft 568 as also discussed above with respect to FIGS. 4A-4B.

In one example, the ablation elements (e.g., ablation elements 572) are placed at the ostium of the pulmonary veins or the ostium of the left atrial appendage. In yet another example, a multitude of electrodes (e.g., ablation elements 572) are provided on the anchor that are capable of delivering radio frequency (RF) energy or high voltage pulses to deliver irreversible electroporation.

All of the above embodiments can optionally be configured to release the anchor from the stabilizer and delivery device. Release from the delivery device could be done mechanically. For example, a ball in socket mechanism could be used to attach the stabilizer to the actuating shaft (e.g., 62) and released by use of an actuator in a user handle of the delivery device (not shown) or the socket itself could be retractable into the catheter and made of a memory shape material such as Nitinol where retraction would cause the socket to change shape and release from the stabilizer. Alternatively, release of the anchor could be accomplished by looping a suture or the like through the anchor material (e.g. metal mesh cage) and threaded back through the catheter. The suture could be cut and removed at a proximal end of the catheter, exterior to the patient, by the clinician to selectively release the anchor. In yet another embodiment, the delivery device could provide an electromagnetic connection between the anchor and the shaft that could be modulated via current injected into the shaft to selectively release the anchor.

Although the present disclosure has been described with reference to preferred embodiments, workers skilled in the art will recognize that changes can be made in form and detail without departing from the spirit and scope of the present disclosure.

What is claimed is:

1. A method of stabilizing a catheter during transseptal access of a left atrium of a heart of a patient the method comprising the steps of:
   delivering a delivery device through a vascular system of the patient to position the delivery device within a septal wall, the delivery device including:
      a catheter including a plurality of lumens; and
      a first stabilizer positioned within a first lumen of the plurality of lumens of the catheter during delivery, the first stabilizer including a first anchor secured to a first shaft, the first anchor having a delivery position during delivery, wherein the first anchor has a first diameter in the delivery position;
   deploying the first stabilizer from the catheter to a deployed position such that the first anchor engages a first pulmonary vein, wherein the first anchor has a second diameter in the deployed position, the second diameter being greater than the first diameter; and advancing a prosthesis through a second lumen of the plurality of lumens of the catheter and into the left atrium.

2. The method of claim 1, wherein the catheter includes a third lumen in which a second stabilizer is positioned and the method further includes the step of deploying a second anchor of the second stabilizer to engage a second pulmonary vein.

3. The method of claim 1, wherein the method further includes the step of detaching the first anchor from the first shaft.

4. The method of claim 1, wherein the first stabilizer is configured to be non-occluding.

5. The method of claim 1, wherein the first stabilizer is a metal cage.

6. The method of claim 1, wherein the first anchor includes an ablation element, the method further comprising the step of ablating tissue adjacent the first anchor.

7. The method of claim 6, wherein the first anchor includes a plurality of ablation elements spaced longitudinally along the first anchor.

8. The method of claim 1, wherein the first anchor is inflated to engage the first pulmonary vein.

9. The method of claim 1, wherein the first anchor is secured to an actuator shaft; the method further comprising the step of adjusting the position of the actuator shaft to vary a diameter of the first anchor.

10. The method of claim 1, wherein the delivery device includes a plurality of tension members that can vary a diameter of the first anchor.

11. A method of stabilizing a catheter during transseptal access of a left atrium of a heart of a patient; the method comprising the steps of:

delivering a delivery device through a vascular system of the patient to position the delivery device within a septal wall, the delivery device including:

a catheter including a plurality of lumens; and a stabilizer positioned within a first lumen of the plurality of lumens of the catheter during delivery, the stabilizer including an anchor secured to a shaft, the anchor having a delivery position during delivery, wherein the anchor has a first diameter in the delivery position;

deploying the stabilizer from the catheter to a deployed position such that the anchor engages a left atrial appendage, wherein the anchor has a second diameter in the deployed position, the second diameter being greater than the first diameter; and advancing a prosthesis through a second lumen of the plurality of lumens of the catheter and into the left atrium.

12. The method of claim 11, further comprising detaching the anchor from the shaft.

13. The method of claim 11, wherein the anchor is a metal cage.

14. The method of claim 11, wherein the anchor includes an ablation element, the method further comprising ablating tissue adjacent the anchor.

15. The method of claim 14, wherein the anchor includes a plurality of ablation elements spaced longitudinally along the anchor.

16. The method of claim 11, wherein the anchor is inflated to engage the left atrial appendage.

17. The method of claim 11, wherein the anchor is secured to an actuator shaft, the method further comprising adjusting the position of the actuator shaft to vary a diameter of the anchor.

18. The method of claim 11, wherein the delivery device includes a plurality of tension members that can vary a diameter of the anchor.

19. The method of claim 11, further comprising:

detaching the anchor from the shaft; and withdrawing the delivery device such the anchor remains in the left atrial appendage as a plug to occlude the left atrial appendage.

\* \* \* \* \*